United States Patent [19]

Cricchio

[11] 4,169,834
[45] Oct. 2, 1979

[54] RIFAMYCIN DERIVATIVES

[75] Inventor: Renato Cricchio, Varese, Italy

[73] Assignee: Gruppo Lepetit S.p.A., Milan, Italy

[21] Appl. No.: 888,890

[22] Filed: Mar. 22, 1978

[30] Foreign Application Priority Data

Apr. 20, 1977 [GB] United Kingdom ............ 16333/77

[51] Int. Cl.² .......................................... C07D 513/18
[52] U.S. Cl. ............................. 260/239.3 P; 424/270
[58] Field of Search ................................. 260/239.3 P

[56] References Cited

U.S. PATENT DOCUMENTS 3,847,901  11/1974  Cricchio ...................... 260/239.3 P
4,042,683  8/1977   White et al. ........................ 424/117

FOREIGN PATENT DOCUMENTS 832921   12/1975  Belgium ............................ 260/239.3 P
2537902  3/1976   Fed. Rep. of Germany .... 260/239.3 P
2548148  5/1976   Fed. Rep. of Germany .... 260/239.3 P Primary Examiner—John M. Ford
Assistant Examiner—Robert T. Bond
Attorney, Agent, or Firm—James W. Ambrosius

[57] ABSTRACT

A process for preparing 4-deoxy-thiazolo[5,4-c]rifamycin SV derivatives of the following general formula

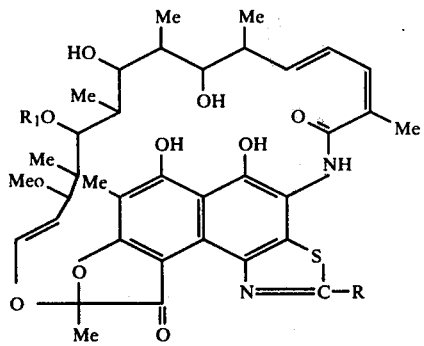

wherein R represents hydrogen or a straight or branched alkyl chain containing from 1 to 10 carbon atoms, $R_1$ is selected from hydrogen and acetyl.

Compounds of formula I above, wherein R is a straight or branched alkyl chain containing from 1 to 10 carbon atoms, $R_1$ is selected from hydrogen and acetyl. These compounds possess antimicrobial utility.

11 Claims, No Drawings

RIFAMYCIN DERIVATIVES

BACKGROUND OF THE INVENTION

The compound of formula I above wherein R is hydrogen and $R_1$ is acetyl is known as rifamycin P. It is described in U.S. Pat. No. 4,042,683 which also reports its preparation by fermentation of *Nocardia Mediterranea* strains ATCC 31064, 31065, 31066.

SUMMARY OF THE INVENTION

The present invention refers to a chemical process for preparing 4-deoxythiazolo[5,4-c]rifamycin SV derivatives of the general formula

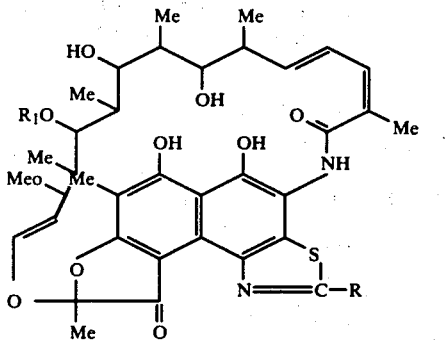

wherein R represents hydrogen or a straight or branched alkyl chain containing from 1 to about 10 carbon atoms and $R_1$ is selected from hydrogen and acetyl. Representative members of the above mentioned alkyl chain are methyl, ethyl, propyl, isopropyl, butyl, sec.-butyl, isobutyl, tert.-butyl, pentyl, isopentyl, neopentyl, hexyl, 2-ethylbutyl, 2-methylpentyl, 3-methylpentyl, 2,3-dimethylbutyl, heptyl, 2-ethylpentyl, 3-ethylpentyl, 2-methylhexyl, 2,3-dimethylpentyl, 2,4-dimethylpentyl, octyl, 2-methylheptyl, 3-methylheptyl, 4-methylheptyl, 3-ethylhexyl, 2,3,4-trimethylpentyl, 3,4-dimethylhexyl, 2-methyl-3-ethylpentyl, nonyl, 2-methyloctyl, 3-methyl-4-ethylhexyl, 3,3,4-trimethylhexyl, 3,4,5-trimethylhexyl, 4-methyloctyl, 4-ethylheptyl, decyl, 5-methylnonyl, 3-methyl-2-ethylheptyl, 1-methylnonyl, 2,3,5-trimethylheptyl, 3-methyl-4-ethylheptyl, 2,2,3,3-tetramethylhexyl, 4-propylheptyl, 3,3-dimethyloctyl, 4-ethyloctyl and 2,4-dimethyl-3-ethylhexyl.

The invention also refers to the compounds of formula I wherein R is a straight or branched alkyl group containing from 1 to about 10 carbon atoms and $R_1$ is selected from hydrogen and acetyl. The compounds possess antimicrobial utility.

A preferred group of compounds comprises those compounds of formula I wherein R is a straight or branched alkyl chain containing from 1 to about 6 carbon atoms and $R_1$ is selected from hydrogen and acetyl.

A most preferred group of compounds comprises those compounds of formula I wherein R is a straight or branched alkyl chain containing from 1 to about 6 carbon atoms and $R_1$ is acetyl.

The compound of formula I wherein R is hydrogen and $R_1$ is acetyl corresponds to the natural product defined in U.S. Pat. No. 4,042,683 as rifamycin P. This microbiologically active metabolite was obtained together with other natural products by fermenting strains of *Nocardia Mediterranea* identified through the following ATRCC numbers: 31064, 31065 and 31066.

Accordingly, a further scope of the invention is a new and convenient route for preparing the known antibiotic substance rifamycin P.

The process of the invention involves the condensation of rifamycin S (or the corresponding 25-desacetyl derivative) with a suitable thioaminoacid according to the following scheme:

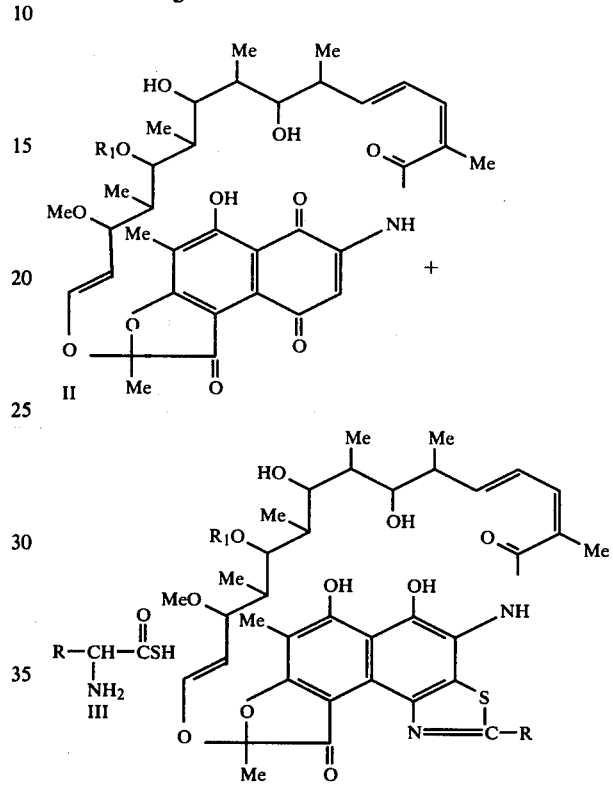

$R_1 = CH_3CO \longrightarrow$ rifamycin S $R_1 = H \longrightarrow$ 25-desacetyl-rifamycin S In the actual practice, the process of the invention is carried out simply by dissolving a molar proportion of rifamycin S or its 25-desacetyl derivative in a suitable organic solvent, such as, for instance, a lower alkanol containing from 1 to 4 carbon atoms, a lower halogenated hydrocarbon containing from 1 to 2 carbon atoms, ethyl acetate, dioxane, tetrahydrofuran and analogs, and adding to this solution an amount of the selected thioaminoacid of formula III corresponding to from about 1 to about 2 molar equivalents over the starting rifamycin of formula II. An amount of a tertiary organic nitrogen containing base corresponding to about 2 molar proportions over the starting rifamycin of formula II can be added to the reaction mixture in order to favor the formation of the desired end compounds.

Suitable amines which can be employed are trimethylamine, triethylamine, pyridine, pycoline, quinoline, isoquinoline and analogs. Though these amines impart to the solution an alkaline pH, it has been found that the reaction course is not affected by the pH of the medium, as good yields of compounds of formula I are obtained also by operating both under neutral or acidic conditions. The reaction mixture is then allowed to stand for from about 2 to about 10 hours at a temperature from between about room temperature and about 50° C. until the investigation by thin layer chromatography shows the disappearance of rifamycin S, the presence of a new spot with a $R_f$ value of 0.8 and the spot due to rifamycin SV with Rf=0.05. The desired end compounds of formula II are finally recovered and purified by means of the usual chemical procedures.

Such procedures comprise the evaporation to dryness of the reaction solution, purification of the residue by column chromatography and final recrystallization from suitable solvents.

As stated above, the compounds of formula I wherein R represents a straight or branched alkyl group containing from 1 to 10 carbon atoms, which are 4-deoxy-2'-alkyl-thiazolo[5,4-c]rifamycin SV derivatives and are an object of the present invention, possess antimicrobial utility. More exactly, they display a broad spectrum in vitro antibacterial activity against gram-positive and gram-negative microorganisms as well as mycobacteria as it can be seen from the hereinbelow reported table which shows the minimum inhibiting concentrations (MIC) of some representative members of the compounds of the invention. The MIC is expressed as µg/ml.

TABLE (MIC)

| Strain | Compound of Example | | | | | | |
|---|---|---|---|---|---|---|---|
|  | 1 | 2 | 3 | 4 | 5 | 6 | 8 |
| *Staph. Aureus* | 0.0004 | 0.00078 | 0.00078 | 0.00078 | 0.00078 | 0.0012 | 0.02 |
| *Staph. Aureus* Tour | 0.00078 | 0.0031 | 0.00156 | 0.00156 | 0.001 | 0.0031 | 0.1 |
| *Strept. haemolyticus* | 0.012 | 0.0031 | 0.0031 | 0.012 | 0.001 | 0.012 | 0.1 |
| *Strept. faecalis* | 0.0062 | 0.0031 | 0.00156 | 0.012 | 0.0062 | 0.012 | 0.4 |
| *Strept. pneumoniae* | 0.0062 | 0.0062 | 0.00078 | 0.012 | 0.0062 | 0.012 | 0.1 |
| *Proteus vulgaris* | 6.25 | 1.56 | 3.12 | 6.25 | 3.12 | 3.12 | 0.78 |
| *Escherichia coli* | 12.5 | 12.5 | 12.5 | 12.5 | 12.5 | 12.5 | 6.25 |
| *Kleb. pneumoniae* | 25.0 | 25.0 | 25.0 | 25.0 | 50.0 | 25 | 12.5 |
| *Pseud. aeruginosa* | 12.5 | 25.0 | 12.5 | 12.5 | 12.5 | 12.5 | 12.5 |
| *Myc. Tub.* $H_{37}R_v$ | 0.31 | 0.62 | 0.62 | 0.31 | 0.15 | 1.2 | 0.6 |

The 4-deoxy-2'-alkyl-thiazolo[5,4-c]rifamycin SV derivatives of the present invention are also effective against rifampicin resistant *Staphylococcus aureus* strains and possess an outstanding in vivo activity against experimental infection by *Staphylococcus aureus* when administered both per os and subcutaneously. This in vivo activity, expressed as an $ED_{50}$, may vary from about 0.3 to about 1 mg/kg per os and from about 0.1 to about 0.4 mg/kg subcutaneoulsy.

The following Examples further illustrate the invention.

EXAMPLE 1

4-Deoxy-2'-ethyl-thiazolo[5,4-c]rifamycin SV (A) To a solution of 7 g. (0.01 mole) of rifamycin S in 1000 ml of ethanol 2.8 g. of triethylamine and 1.5 g (0.0126 mole) of α-amino-thiobutyric acid were added and the resulting solution was kept at about 36° C. for 3 hours until complete disappearance of rifamycin S (investigation by thin layer chromatography). The reaction mixture was then brought to dryness and the obtained residue, after dissolving in 15 ml of CHCl₃, was chromatographed through silica-gel by eluting with a mixture of chloroform/methanol=99/1 (v/v). The fractions containing the title compound were collected, concentrated to dryness and the obtained residue, after dissolving in ethyl acetate, was poured under agitation into 150 ml of hexane. A precipitate crystallized out which was collected and dried. Yield 2.0 grams. M.p. 160–65° C.

| Elemental analysis | %C | % H | % N | % S |
|---|---|---|---|---|
| Calculated for $C_{40}H_{50}N_2O_{11}S$ | 62.64 | 6.57 | 3.65 | 4.18 |
| Found | 61.76 | 6.68 | 3.44 | 3.96 |

U.V. and visible absorption bands buffer pH7.38

| λ max (mµ) | $E_{1cm}^{1\%}$ |
|---|---|
| 410 | 166 |
| 299 | 329 |
| 260 | 420 |
| 225 | 557 |

(B) The title compound was also prepared by dissolving the above amounts of rifamycin S and α-amino-thiobutyric acid in 1000 ml of methanol and adding 100 ml. of phosphate buffer pH 4.6. The resulting solution is allowed to stand for 9 hours at room temperature. Yield 28%

EXAMPLES 2–8

The following 4-deoxy-2'-alkyl-thiazolo[5,4-c]rifamycin SV derivatives were prepared substantially as described in Example 1(A), starting from a rifamycin compound of formula II and a suitable thioamino acid of formula III.

EXAMPLE 2

4-Deoxy-2'-methyl-thiazolo[5,4-c]rifamycin SV, from, rifamycin S and α-amino-thiopropionic acid. Yield 32%. M.p. 157–60° C. (with decomposition).

| Elemental analysis | %C | % H | % N | % S |
|---|---|---|---|---|
| Calculated for $C_{39}H_{48}N_2O_{11}S$ | 62.22 | 6.42 | 3.72 | 4.26 |
| Found | 61.03 | 6.36 | 3.61 | 4.08 |

U.V. and visible absorption bands buffer pH 7.38

| λ max (mµ) | $E_{1cm}^{1\%}$ |
|---|---|
| 408 | 172 |
| 297 | 316 |
| 257 | 419 |

EXAMPLE 3

4-Deoxy-2'-propyl-thiazolo[5,4-c]rifamycin SV, from rifamycin S and α-amino-thiovalerianic acid. Yield 26%. M.p. 168–70° C.

| Elemental analysis | % C | % H | % N | % S |
|---|---|---|---|---|
| Calculated for $C_{41}H_{52}N_2O_{11}S$ | 63.09 | 6.66 | 3.59 | 4.11 |
| Found | 62.15 | 6.66 | 3.46 | 3.82 |

-continued

U.V. and visible absorption bands

Buffer pH 7.38

| λ max (mμ) | $E_{cm}^{1\%}$ |
|---|---|
| 404 | 176 |
| 298 | 353 |
| 258 | 455 |

The title compound was also obtained with a 29% yield according to the procedure outlined in Example 1(B), with the only difference that phosphate buffer pH 6.8 was used instead of phosphate buffer pH 4.6.

EXAMPLE 4

4-Deoxy-2'-isopropyl-thiazolo[5,4-c]rifamycin SV, from rifamycin S and α-amino-3-methyl-thiobutyric acid. Yield 28%. M.p. 168–72° C.

| Elemental analysis | % C | % H | % N | % S |
|---|---|---|---|---|
| Calculated for $C_{41}H_{52}N_2O_{11}S$ | 63.09 | 6.66 | 3.59 | 4.11 |
| Found | 62.22 | 6.72 | 3.49 | 4.02 |

U.V. and visible absorption bands buffer pH 7.38

| λ max (mμ) | $E_{cm}^{1\%}$ |
|---|---|
| 410 | 162.5 |
| 299 | 322.4 |
| 260 | 421 |
| 225 | 544 |

EXAMPLE 5

4-Deoxy-2'-isobutyl-thiazolo[5,4-c]rifamycin SV, from rifamycin S and α-amino-4-methyl-thiovalerianic acid. Yield 31%. M.p. 170–75° C.

| Elemental analysis | % C | % H | % N | % S |
|---|---|---|---|---|
| Calculated for $C_{42}H_{54}N_2O_{11}S$ | 63.46 | 6.85 | 3.52 | 4.03 |
| Found | 62.45 | 7.05 | 3.88 | 3.80 |

U.V. and visible absorption bands buffer pH 7.38

| λ max (mμ) | $E_{cm}^{1\%}$ |
|---|---|
| 410 | 155 |
| 299 | 260 |
| 260 | 398 |
| 225 | 515 |

EXAMPLE 6

4-Deoxy-2'-hexyl-thiazolo[5,4-c]rifamycin SV, from rifamycin S and α-amino-thiooctanoic-acid. Yield 27%. M.p. 148–50° C. (decomposition).

| Elemental analysis | % C | % H | % N | % S |
|---|---|---|---|---|
| Calculated for $C_{44}H_{58}N_2O_{11}S$ | 64.21 | 7.10 | 3.40 | 3.89 |
| Found | 63.12 | 7.31 | 3.58 | 3.42 |

U.V. and visible absorption bands buffer pH 7.38

| λ max (mμ) | $E_{cm}^{1\%}$ |
|---|---|
| 410 | 143 |
| 298 | 278 |
| 257 | 356 |
| 225 | 427 |

EXAMPLE 7

4-Deoxy-thiazolo[5,4-c]rifamycin SV (rifamycin P), from rifamycin S and α-aminothioacetic acid. Yield 33%. M.p.: the compound melts above 190° C. with decomposition.

| Elemental analysis | % C | % H | % N | % S |
|---|---|---|---|---|
| Calculated for $C_{38}H_{46}N_2O_{11}S$ | 61.77 | 6.27 | 3.79 | 4.34 |
| Found | 60.27 | 6.35 | 3.68 | 4.19 |

U.V. and visible absorption bands

| methanol | | 0,1 N HCl | |
|---|---|---|---|
| λ max (mμ) | $E_{cm}^{1\%}$ | λ max (mμ) | $E_{cm}^{1\%}$ |
| 408 | 176 | 416 | 175 |
| 350 | shoulder | 303 | 292 |
| 300 | 314 | 231 | 450 |
| 268 | 349 | | |
| 228 | 424 | | |

Infrared Spectrum The most significant absorption peaks in nujol occur at the following frequencies (cm.$^{-1}$): 3700–3200 (m, br); 3120–3080 (w); 3000–2850 (vs); 1465 (s); 1380 (br):Nujol; 1725 (m); 1640 (m,br); 1580 (m); 1520 (m); 1325 (m); 1250 (s,br); 1155 (m); 1130 (w); 1070 (m,br); 1045 (w); 975 (m); 950 (m); 920 (w); 880 (m); 805 (w); 760 (w): 730 (w).

The identity with rifamycin P obtained by fermentation was also confirmed by the chromatographic behavior in different solvent systems and by mass and nuclear magnetic resonance spectromethy.

EXAMPLE 8

25-Desacetyl-4-deoxy-thiazolo[5,4-c]rifamycin SV, from 25-desacetyl-rifamycin S and α-amino-thioacetic acid. M.p.: the compound melts above 155° C. with decomposition.

| Elemental analysis | % C | % H | % N | % S |
|---|---|---|---|---|
| Calculated for | 62.05 | 6.36 | 4.02 | 4.60 |
| Found | 61.98 | 6.32 | 4.04 | 4.56 |

The U.V. spectrum is practically identical with that of rifamycin P. According to the procedure described in the above Examples the following 4-deoxy-2'-alkyl-thiazolo[5,4-c]rifamycin SV derivatives can be prepared.

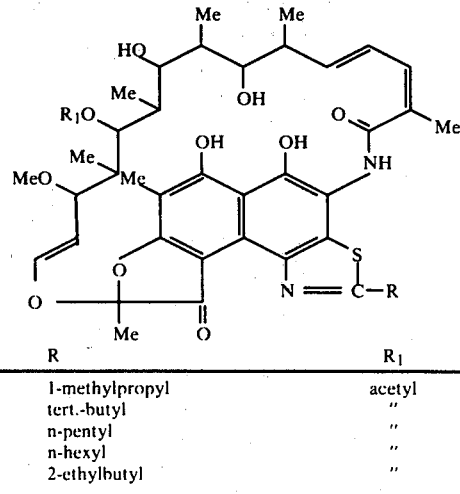

| R | $R_1$ |
|---|---|
| 1-methylpropyl | acetyl |
| tert.-butyl | " |
| n-pentyl | " |
| n-hexyl | " |
| 2-ethylbutyl | " |

-continued

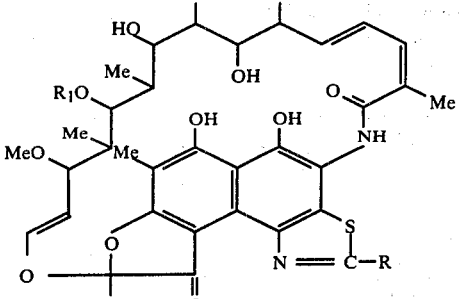

| R | R₁ |
|---|---|
| 2-methylpentyl | '' |
| 2,2-dimethylbutyl | '' |
| n-heptyl | '' |
| n-octyl | '' |
| n-nonyl | '' |
| n-decyl | '' |

The starting thioaminoacids of formula II were prepared according to the procedure reported by T. Wieland and K. E. Euler in Chem. Ber., 91, 2305, 1958 and R. S. Dewey et al. in Journ. Org. Chem., 36, 49, 1971. The melting points of these thioamino acids are hereinbelow reported

| Acid | M.p. °C. |
|---|---|
| α-amino-thiobutyric | 250° dec. |
| α-amino-thiopropionic | 190° |
| α-amino-thiovalerianic | 200° |
| α-amino-3-methyl-thiobutyric | 300° |
| α-amino-4-methyl-thiovalerianic | 265° dec. |
| α-amino-thioctanoic | 290° dec. |
| α-amino-thioacetic | 160° |

I claim:

1. A process for preparing a 4-deoxy-thiazolo[5,4-c]rifamycin SV of the following formula

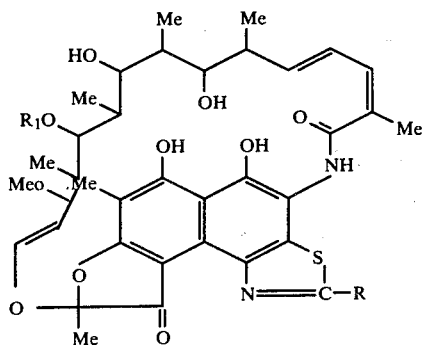

wherein R represents hydrogen or a straight or branched alkyl chain containing from 1 to about 10 carbon atoms and R₁ is selected from hydrogen or acetyl, which comprises condensing a molar proportion of a rifamycin compound of formula

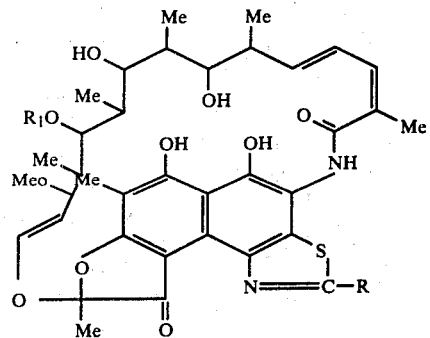

with from about 1 to about 2 molar equivalents of a thioaminoacid of formula

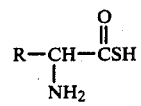

wherein R and R₁ are defined as above, in the presence of an organic solvent for a time varying from about 2 to about 10 hours, at a temperature comprised between room temperature and about 50° C., and recovering the 4-deoxy-thiazolo[5,4-c]rifamycin SV as defined in formula I.

2. A process as defined in claim 1, wherein the organic solvent is a lower alkanol containing from 1 to 4 carbon atoms.

3. A compound of formula

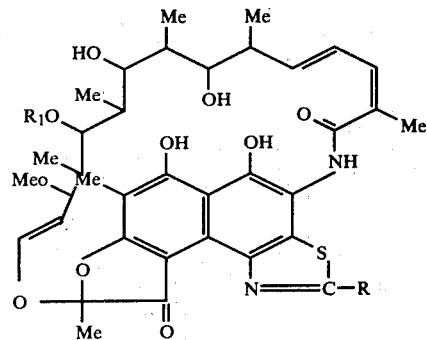

wherein R is a straight or branched alkyl chain containing from 1 to 10 carbon atoms and R₁ is selected from hydrogen or acetyl.

4. A compound as defined in claim 3, wherein R is a straight or branched alkyl chain containing from 1 to 6 carbon atoms and R₁ is selected from hydrogen or acetyl.

5. A compound as defined in claim 3, wherein R is a straight or branched alkyl chain containing from 1 to 6 carbon atoms and R₁ is acetyl.

6. A compound as defined in claim 3, which is 4-deoxy-2'-ethyl-thiazolo[5,4-c]rifamycin SV.

7. A compound as defined in claim 3, which is 4-deoxy-2'-methyl-thiazolo[5,4-c]rifamycin SV.

8. A compound as in claim 3, which is 4-deoxy-2'-propyl-thiazolo[5,4-c]rifamycin SV.

9. A compound as in claim 3, which is 4-deoxy-2'-isopropyl-thiazolo[5,4-c]rifamycin SV.

10. A compound as in claim 3, which is 4-deoxy-2'-isobutyl-thiazolo[5,4-c]rifamycin SV.

11. A compound as in claim 3, which is 4-deoxy-2'-hexyl-thiazolo[5,4-c]rifamycin SV.

* * * * *

UNITED STATES PATENT AND TRADEMARK OFFICE
CERTIFICATE OF CORRECTION

PATENT NO. : 4,169,834
DATED : October 2, 1979
INVENTOR(S) : Renato Cricchio

It is certified that error appears in the above-identified patent and that said Letters Patent are hereby corrected as shown below:

Page 1, under Abstract, formula should read as follows:

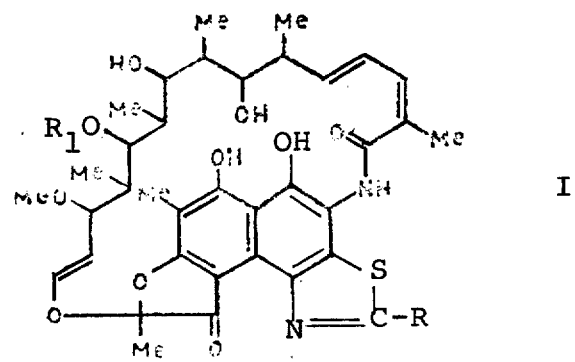

Column 1, under Summary of the Invention, lines 15-30, formula should read as follows:

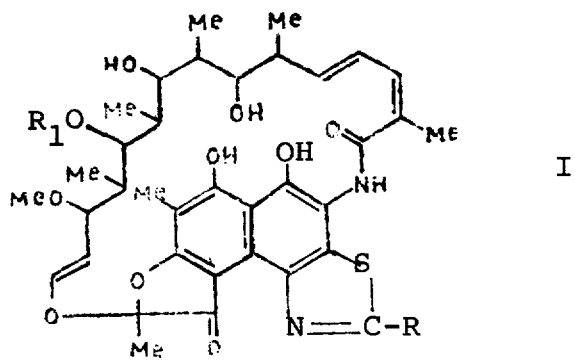

UNITED STATES PATENT AND TRADEMARK OFFICE
CERTIFICATE OF CORRECTION

PATENT NO. : 4,169,834
DATED : October 2, 1979
INVENTOR(S) : Renato Cricchio

It is certified that error appears in the above-identified patent and that said Letters Patent are hereby corrected as shown below:

Column 2, line 2, "ATRCC" should read --ATCC--.

Column 4, line 44, "from," should read --from--.

Column 6, line 21, after Infrared Spectrum a new paragraph should start.

Column 7, line 40, should read as follows, --α-amino-thiooctanoic     290° dec.--.

Column 7, Claim 1, the first formula should read as follows:

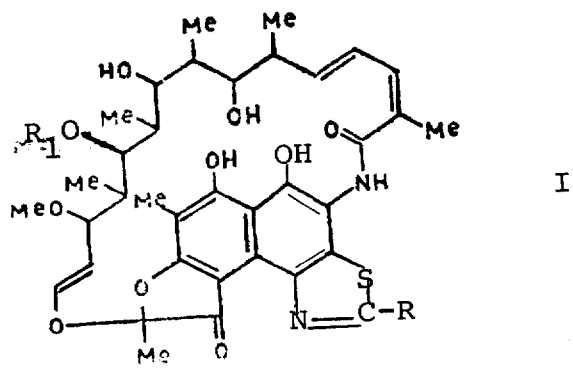

I

UNITED STATES PATENT AND TRADEMARK OFFICE
CERTIFICATE OF CORRECTION

PATENT NO. : 4,169,834

DATED : October 2, 1979

INVENTOR(S) : Renato Cricchio

It is certified that error appears in the above-identified patent and that said Letters Patent are hereby corrected as shown below:

Column 8, Claim 1, second formula, should read as follows:

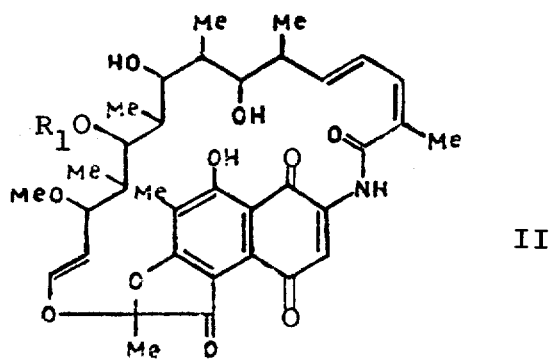

II

UNITED STATES PATENT AND TRADEMARK OFFICE
CERTIFICATE OF CORRECTION

PATENT NO. : 4,169,834

DATED : October 2, 1979

INVENTOR(S) : Renato Cricchio

It is certified that error appears in the above-identified patent and that said Letters Patent are hereby corrected as shown below:

Column 8, line 35, Claim 3, formula should read as follows:

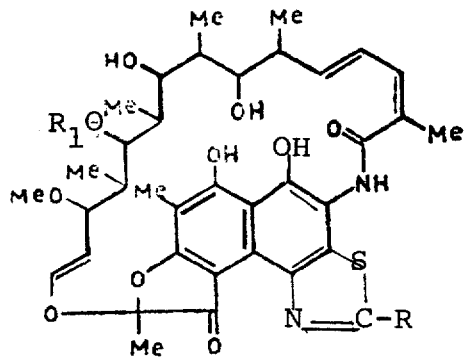

Signed and Sealed this

Fifteenth Day of January 1980

[SEAL]

Attest:

SIDNEY A. DIAMOND

Attesting Officer    Commissioner of Patents and Trademarks